United States Patent [19]

Snowling et al.

[11] 4,189,483
[45] Feb. 19, 1980

[54] PESTICIDAL COMPOUNDS, COMPOSITIONS AND PROCESSES

[75] Inventors: Geoffrey D. Snowling, Clarke; John M. Cox, Wokingham; Raymond A. Burrell, Camberley; Margaret C. Shephard, Maidenhead, all of England

[73] Assignee: Imperial Chemical Industries Limited, London, England

[21] Appl. No.: 888,388

[22] Filed: Mar. 20, 1978

[30] Foreign Application Priority Data

Mar. 23, 1977 [GB] United Kingdom ............... 12211/77

[51] Int. Cl.$^2$ ............................. A01N 9/00; A01N 9/22
[52] U.S. Cl. ............................ 424/251; 71/92; 544/255
[58] Field of Search ............... 424/281; 544/255; 71/92

[56] References Cited

U.S. PATENT DOCUMENTS 3,778,438  12/1973  Simpson .............................. 544/255
3,853,877  12/1974  Simpson .............................. 424/250

FOREIGN PATENT DOCUMENTS 2350387  4/1974  Fed. Rep. of Germany.

OTHER PUBLICATIONS

Taylor et al., J. Org. Chem. 29(8), 2116–2120 (1964).

Primary Examiner—Allen J. Robinson
Attorney, Agent, or Firm—Cushman, Darby & Cushman

[57] ABSTRACT

A process for combating pests, especially fungi, which comprises applying to plants, seeds, or their loci, an isoxazolo [5,4-d] pyrimidine derivative having the formula:

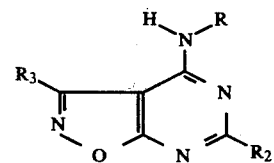

or a salt or optical isomer thereof, wherein R is alkyl or aralkyl, either optionally-substituted; $R_2$ is hydrogen or alkyl; $R_3$ is alkyl, aryl, alkylthio, alkanesulphonyl, alkoxy, aryloxy, cyano or optionally-substituted amino.

4 Claims, No Drawings

PESTICIDAL COMPOUNDS, COMPOSITIONS AND PROCESSES

This invention relates to isoxazolo [5,4-d] pyrimidine derivatives useful as pesticides, to a process for preparing them, to pesticidal compositions containing them, and to a method of combating pests using them.

The invention provides a process for combating pests which comprises applying to plants, seeds, or their loci, an isoxazolo [5,4-d] pyrimidine derivative having the formula:

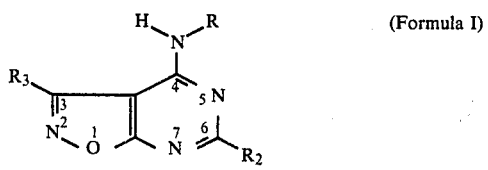

(Formula I)

or a salt or optical isomer thereof, wherein R is alkyl or aralkyl, either optionally-substituted; $R_2$ is hydrogen, alkyl or halogen; $R_3$ is alkyl, aryl, alkylthio, alkanesulphonyl, alkoxy, aryloxy, cyano or optionally-substituted amino.

In a preferred aspect the invention provides a process as defined above wherein in the general formula (formula I) R is alkyl, alkoxyalkyl, or aralkyl, each optionally-substituted, $R_2$ is hydrogen or alkyl; $R_3$ is alkyl or aryl.

When R is a substituted alkyl or aralkyl group the substituent or substituents may be one or more carboxyl, hydroxy, cyano, furyl, pyridyl, alkoxy, mono- or di-alkylamino, phenyl, or halo-, alkyl- or alkoxy-substituted phenyl groups. Preferred alkyl groups are those containing 2 or more, especially 2 to 13 carbon atoms, and particularly from 3 to 10 carbon atoms. When R is an aralkyl group a preferred groups are benzyl and α-lower alkyl-substituted benzyl, especially α-methylbenzyl.

The term alkoxyalkyl is intended to include oxygen-interrupted alkylene chains (see, for example, compounds nos 31 and 33 of Table I hereinafter), especially up to 13 carbon atoms.

When $R_2$ is alkyl it may be methyl or ethyl, but methyl is especially preferred. When $R_2$ is halogen, chlorine and fluorine are preferred over bromine and iodine.

When $R_3$ is alkyl it may be, for example, methyl or ethyl, especially methyl. Other preferred values for $R_3$ are methoxy, methanesulphonyl, methylthio and phenyl.

In a further, more preferred aspect, therefore, the invention provides a process as defined above wherein R in the general formula (Formula I) is alkyl having from 3 to 10 carbon atoms or aralkyl, either optionally-substituted, or alkoxyalkyl having up to 13 carbon atoms; $R_2$ is hydrogen or methyl; $R_3$ is methyl, ethyl, methoxy, methanesulphonyl, methylthio or phenyl.

In a yet further aspect the invention provides isoxazolo [5,4-d] pyrimidine derivatives having the formula:

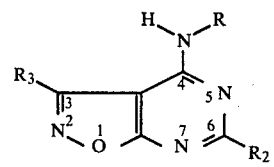

and salts and optical isomers thereof, wherein R is optionally-substituted alkyl having 2 or more carbon atoms, alkoxyalkyl or optionally-substituted aralkyl, $R_2$ is hydrogen or alkyl; $R_3$ is alkyl, alkylthio, alkanesulphonyl, alkoxy, cyano or optionally-substituted amino.

Specific derivatives according to the invention are listed below in Table I. These correspond to Formula I above, the values for R, $R_2$ and $R_3$ being given.

All these specific compounds, with the exception of Compound No 18, are novel and fall within the scope of this invention. Compound No 18 is known from Chemical Abstracts 61:8307C. The compound substituted of position 3 with phenyl (i.e. $R_3$ is $C_6H_5$) and at position 4 with $NHCH_3$ (i.e. R is $CH_3$) is also known from Chemical Abstracts 61:8307C.

Other known compounds are disclosed in German Offenlegungschrift No 2350387.

TABLE I

| COMPOUND NO | R | $R_2$ | $R_3$ | MELTING POINT °C. [BOILING POINT (BATH)/ PRESSURE (mm Hg )] |
|---|---|---|---|---|
| 1 | —CH(CH$_3$)$_2$ | H | CH$_3$ | 168°–170° |
| 2 | —CH(CH$_3$)CH$_2$CH$_3$ | H | CH$_3$ | 115°–117° |
| 3 | —CH(CH$_3$)C$_6$H$_5$ | H | CH$_3$ | 124°–126° |
| 4 | —CH(CH$_3$)(CH$_2$)$_4$CH$_3$ | H | CH$_3$ | 84°–86° |
| 5 | —CH(CH$_3$)(CH$_2$)$_2$CH$_3$ | H | CH$_3$ | 96°–98° |
| 6 | —CH(CH$_3$)C$_6$H$_5$ | H | C$_2$H$_5$ | 136°–137° |
| 7 | —CH(CH$_3$)(CH$_2$)$_2$CH$_3$ | H | C$_2$H$_5$ | 89°–90° |
| 8 | —(CH$_2$)$_9$CH$_3$ | H | C$_2$H$_5$ | 73°–74° |

TABLE I-continued

| COMPOUND NO | R | R$_2$ | R$_3$ | MELTING POINT °C. [BOILING POINT (BATH)/ PRESSURE (mm Hg)] |
|---|---|---|---|---|
| 9 | —CH(CH$_3$)CH$_2$CH$_3$ | H | C$_2$H$_5$ | 116°–117° |
| 10 | —CH(CH$_3$)(CH$_2$)$_4$CH$_3$ | H | C$_2$H$_5$ | 67°–68° |
| 11 | —CH(CH$_3$)(CH$_2$)$_5$CH$_3$ | H | CH$_3$ | 97°–98° |
| 12 | —CH(CH$_3$)(CH$_2$)$_3$CH$_3$ | H | CH$_3$ | 48°–51° |
| 13 | —CH(CH$_3$)(CH$_2$)$_2$CH$_3$ | H | C$_6$H$_5$ | 71°–72° |
| 14 | —(CH$_2$)$_9$CH$_3$ | H | C$_6$H$_5$ | 88°–89° |
| 15 | —CH(CH$_3$)CH$_2$CH$_3$ | H | C$_6$H$_5$ | 112°–113° |
| 16 | —CH(CH$_3$)CH$_2$CH$_3$ | CH$_3$ | CH$_3$ | 101° |
| 17 | —CH(CH$_3$)$_2$ | H | SCH$_3$ | 104° |
| 18 | —CH$_3$ | H | CH$_3$ | 236° |
| 19 | —CH(CH$_3$)(CH$_2$)$_2$CH$_3$ | H | SCH$_3$ | 49° [140°/0.01] |
| 20 | —CH(CH$_3$)(CH$_2$)$_5$CH$_3$ | H | SCH$_3$ | [160°/0.01] |
| 21 | —CH(CH$_3$)$_2$ | H | SO$_2$CH$_3$ | 113° |
| 22 | —CH(CH$_3$)$_2$ | H | OCH$_3$ | 106° |
| 23 | —CH(CH$_3$)$_2$ | CH$_3$ | CH$_3$ | 149° |
| 24 | —CH(CH$_3$)(CH$_2$)$_2$CH$_3$ | CH$_3$ | CH$_3$ | 76° |
| 25 | —CH(CH$_3$)(CH$_2$)$_3$OCH$_2$CH$_3$ | H | CH$_3$ | [170°/0.06] |
| 26 | —CH(CH$_3$)C$_6$H$_5$ | CH$_3$ | CH$_3$ | 101° |
| 27 | —CH(CH$_3$)C$_6$H$_5$ S-configuration | H | CH$_3$ | 147° |
| 28 | —CH(CH$_3$)C$_6$H$_5$ R-configuration | H | CH$_3$ | 145° |
| 29 | —(CH$_2$)$_2$CH(CH$_3$)$_2$ | H | CH$_3$ | 133° |
| 30 | —CH(CH$_3$)(CH$_2$)$_5$CH$_3$ | CH$_3$ | CH$_3$ | [175°/0.05] |
| 31 | —CH(CH$_3$)(CH$_2$)$_3$O(CH$_2$)$_2$O(CH$_2$)$_3$CH$_3$ | H | CH$_3$ | [200°/0.08] |
| 32 | —CH(CH$_3$)(CH$_2$)$_3$O(CH$_2$)$_3$CH$_3$ | CH$_3$ | H | [185°/0.06] |
| 33 | —CH(CH$_3$)(CH$_2$)$_3$O(CH$_2$)$_2$O(CH$_2$)$_2$O(CH$_2$)$_3$CH$_3$ | H | CH$_3$ | [240°/0.1] |

The isoxazolo [5,4-d] pyrimidine compounds of the invention can be made, for example, either by:

(a) treating an appropriately substituted 4-cyano-5-aminooxazole successively with an orthoester, an amine and, if necessary, a base to aid cyclisation and Dimroth rearrangement, or (b) reacting an isoxazolo [5,4-d] pyrimidine containing a labile function (e.g. halo) at the 4-position with an amine or a salt thereof, or (c) subjecting a compound prepared as described above under (a) or (b) to further reaction for example oxidising an alkylthio group to an alkanesulphonyl group, displacing a labile function (e.g. alkanesulphonyl, halo, alkylthio) at the 3- or 6-positions with a nucleophile (e.g. alkoxide, amines).

The derivatives and compositions containing them are active against a wide range of fungal diseases, particularly, for example against:

(a) *Phytophthora infestans* (late blight) on potatoes and tomatoes
(b) Powdery mildews, for example:
   *Erysiphe graminis* on cereals
   *Sphaerotheca fuliginea* on cucurbits
   *Podosphaera leucotricha* on apples
   *Uncinula necator* on vines
   and other powdery mildews on other hosts
(c) Rusts, for example:
   Puccinia species on cereals and rusts on, for example, coffee plants, apple trees, vegetables, ornamental plants, and other hosts.
(d) Other fungal diseases, for example:
   *Piricularia oryzae* (blast) on rice
   *Botrytis cinera* (grey mould) on vines, strawberries, tomatoes and other hosts
   Plasmopara viticola (downy mildew) on vines
   *Venturia inaequalis* (scab) on apples The invention compounds are also variously active against bacterial and viral infections of plants, especially tomato mosaic virus. Some of them also have acaricidal and insecticidal activity*, nematocidal activity, and exhibit growth regulating effects on plants, and can be used as herbicides at appropriate rates of application.

* especially compounds nos 2, 4, 5 and 12 of Table I above, compound no 12 controlling red spider mites, aphids, houseflies (*Musca domestica*) and caterpillars (Plutella).

The invention compounds also display a broad spectrum of anti-fungal and anti-bacterial activity in vitro and are likely to be active against all main groups of these pathogens. Compound No 2 of Table I is, for example, active against the plant bacterial disease *Xanthomonas oryzae* (rice blight).

The isoxazolo [5,4-d] pyrimidine derivatives may be used as such for anti-fungal purposes but are more conveniently formulated into compositions for such usage.

The invention also provides pesticidal, especially fungicidal, compositions comprising as active ingredient an isoxazolo [5,4-d] pyrimidine derivative as defined in any of the paragraphs above.

The isoxazolo [5,4-d] pyrimidine derivatives and compositions containing them can be used to combat plant fungi and treat plants or seeds in a number of ways, for example they can be applied, formulated or unformulated, directly to the foliage of a plant which is infected or likely to become infected, or they can be applied also to bushes and trees, to soil or to other medium in which plants, bushes or trees are growing or to be planted, or they can be sprayed on, dusted on or applied as a cream or paste formulation. Application can be to any part of the plant, bush or tree, for example to the foliage, stems, branches, seeds or roots, or to soil surrounding the roots.

The term "treating" as used herein refers to all these modes of application and the term "plant" includes seedlings, bushes and trees. Furthermore, the method of the invention includes protectant, prophylactic and eradicant treatment.

The derivatives are preferably used for agricultural and horticultural purposes in the form of compositions. The type of composition used in any instance will depend upon the particular purpose envisaged.

The compositions may be in the form of dusting powders or granules, for example ordinary grains or "slow release" granules wherein the active ingredient is mixed with a solid diluent or carrier, for example, kaolin, bentonite, kieselguhr, dolomite, calcium carbonate, talc, powdered magnesia, Fuller's earth, gypsum, Hewitt's earth, diatomaceous earth and China clay. Compositions for dressing seed may, for example, comprise an agent (for example a mineral oil) for assisting the adhesion of the composition to the seed.

The compositions may also be in the form of dispersible powders or grains comprising a wetting agent to facilitate the dispersion in liquids of the powder or grains which may contain also fillers and suspending agents.

The aqueous dispersion or emulsions may be prepared by dissolving the active ingredient(s) in an organic solvent which may contain wetting, dispersing or emulsifying agent(s) and then adding the mixture so obtained to water which may also contain wetting, dispersing or emulsifying agent(s). Suitable organic solvents are ethylene dichloride, isopropyl alcohol, propylene glycol, diacetone alcohol, toluene, kerosene, methylnaphthalene, xylenes and trichloroethylene.

The compositions for spraying may also be in the form of aerosols wherein the formulation is held in a container under pressure in the presence of a propellant, e.g. fluorotrichloromethane or dichlorodifluoromethane.

By including suitable additive, for example additives for improving the distribution, adhesive power and resistance to rain on treated surfaces, the different compositions can be better adapted for various utilities.

The derivatives can be used in smoke generators and also as mixtures with fertilisers (e.g. nitrogen—or phosphorus—containing fertilisers). Compositions comprising only granules of fertiliser incorporating, for example coated with, the derivative, are preferred.

The invention therefore also provides a fertiliser composition comprising the derivative and a fertiliser.

The compositions may also be in the form of liquid preparations for use as dips or sprays which are generally aqueous dispersions or emulsions containing the active ingredient in the presence of one or more wetting agent(s), dispersing agent(s), emulsifying agent(s) or suspending agent(s). These agents can be cationic, anionic or nonanionic agents. Suitable cationic agents are quaternary ammonium compounds for example, cetyltrimethylammonium bromide.

Suitable anionic agents are soaps, salts of aliphatic monoesters of sulphuric acid (for example sodium lauryl sulphate), and salts of sulphonated aromatic compounds (for example sodium dodecylbenzenesulphonate, sodium, calcium or ammonium lignosulphonate, butylnaphthalene sulphonate, and a mixture of sodium diisopropyl- and triisopropyl-naphthalene sulphonates).

Suitable non-ionic agents are the condensation products of ethylene oxide with fatty alcohols such as oleyl alcohol or cetyl alcohol, or with alkyl phenols such as octylphenol, nonylpyenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example polyvinylpyrrolidone and sodium carboxymethylcellulose), and the vegetable gums (for example gum acacia and gum tragacanth).

The compositions for use as aqueous dispersion or emulsions are generally supplied in the form of a concentrate containing a high proportion of the active ingredient(s), the concentrate to be diluted with water before use. These concentrates often should be able to withstand storage for prolonged periods and after such storage be capable of dilution with water in order to form aqueous preparations which remain homogeneous for a sufficient time to enable them to be applied by conventional spray equipment. The concentrates may conveniently contain 10–85%, generally 25–60%, by weight of the active ingredient(s). When diluted to form aqueous preparations, such preparations may contain varying amounts of the active ingredient(s) depending upon the intended purpose, but an aqueous preparation containing 0.0005% or 0.01% to 10% by weight of active ingredient(s) may be used.

The compositions of this invention can comprise also other compound(s) having biological activity, for example other fungicides such as dithiocarbamates, dinocap, dichlofluanid and the like, as well as stabilising agent(s), for example epoxides (e.g. epichlorhydrin).

The invention is illustrated by the following Examples wherein the temperatures are in °C.

EXAMPLE 1

This Example illustrates the preparation of Compounds nos 1–15, 18, 25 and 27–29 of Table I.

3-Methylbutylamine (1.74 g) was added dropwise to a solution of 4-cyano-5-ethoxymethyleneamino-3-methylisoxazole (3.6 g, prepared as described by E C Taylor and E E Garcia, J. Org. Chem., 1964, 29, 2116) in ethanol (30 ml). The mixture was stirred for ten minutes* at room temperature, treated with a solution of sodium ethoxide (from 0.46 g sodium) in ethanol (10 ml) and refluxed* for four hours. It was then cooled and diluted with water. The precipitate**** was dried and recrystallised from isopropanol to give 3-methyl-4(3-methylbutylamino)isoxazolo [5,4-d] pyrimidine (2.7 g, m.p. 133°), Compound no 29 of Table I.

*The mixture was stirred until starting isoxazole could no longer be detected by thin-layer chromatography. The time required varied with the particular reagents.
**5 N sodium hydroxide solution was used in some cases.
***Stirring at room temperature will suffice in some instances. The time required to complete reaction, as shown by chromatography, varied with the particular reagents.
****In certain cases no solid appeared. The mixture was extracted with ether, washed with water, dried and evaporated. If solid, the residue was recrystallised from a suitable solvent; if liquid, distilled in a bulb-tube apparatus in vacuo. Melting- or boiling-points were as shown in Table I.

The other compounds of this Example were prepared similarly using appropriate amines and 3-substituted-4-cyano-5-aminoisoxazoles. Modifications to the general method may be necessary.

EXAMPLE 2

This Example illustrates the preparation of Compounds nos 31–33 of Table I and provides an alternative procedure to that described in Example 1.

A mixture of 3-methylisoxazolo [5,4-d] pyrimidin-4-(5H)-one (2.0 g, prepared as described by E C Taylor and E E Garcia, J. Org. Chem., 1964, 29, 2116), thionyl chloride (25 ml) and N,N-dimethylformamide (1 ml) was refluxed for one hour, then evaporated in a rotary evaporator. The residue was dissolved in dichloromethane, washed well with ice-cold water, dried and evaporated to give crude chloro derivative (0.70 g). This was dissolved in acetonitrile (1 ml) and treated with 2-amino-6,9,12-trioxahexadecane (0.90 g) and triethylamine (0.42 g). The mixture was refluxed for two hours, diluted with water and extracted with ether. The extracts were washed, dried, evaporated and distilled in a bulb-tube apparatus in vacuo to give Compound no 33 of Table I. [0.80 g, b.p. 240°–250° (bath)/0.1 mm].

Compounds nos 31 and 32 were prepared similarly using the appropriate amine.

EXAMPLE 3

This Example illustrates the preparation of Compounds nos 16, 23, 24, 26 and 30 of Table I.

A mixture of 5-amino-4-carbamoyl-3-methylisoxazole (14.9 g), triethylorthoacetate (112 ml) and acetic anhydride (112 ml) was refluxed for seven hours then evaporated in vacuo. The residue was dissolved in 0.880 ammonia solution (250 ml) and the solution treated with charcoal and filtered. The filtrate was acidified to pH 6 with acetic acid and the precipitate filtered and dried to give 3,6-dimethylisoxazolo [5,4-d] pyrimidin-4(5H)-one (9.8 g, m.p. 275°–280°, decomp.). A mixture of this material (3.2 g), thionyl chloride (30 ml) and N,N-dimethylformamide (1 ml) was refluxed for ten minutes, evaporated in vacuo at ca 50°. The residue was dissolved in dichloromethane, washed well with ice-cold water, dried and evaporated to give crude chloro derivative. A solution of this material in acetonitrile (50 ml) was treated with α-methylbenzylamine (4.84 g, two equivalents) keeping the temperature below 15°. The mixture was stirred for twenty hours at room temperature*, evaporated in vacuo, and distributed between ether and water. The extracts were washed, dried, evaporated and distilled in a bulb-tube apparatus (200°–210°/0.05 mm). The distillate crystallised on trituration with petroleum (b.p. 40°–60°). Recrystallisation from cyclohexane gave Compound no 26 of Table I (0.70 g, m.p. 99°–101°).

*The reaction with the chloro derivative was allowed to proceed until no starting material was present by chromatography. The conditions (temperature and length of reaction) varied with the amine involved.

Compounds nos 16, 23, 24 and 30 were made similarly substituting two molecular equivalents of the appropriate amine in place of α-methylbenzylamine.

EXAMPLE 4

This Example illustrates the preparation of 4-amino-3-methylthioisoxazolo [5,4-d] pyrimidines, Compounds nos 17, 19 and 20 of Table I.

A mixture of 5-amino-4-cyano-3-methylthioisoxazole (30.0 g, prepared as described by R Gompper and W Topfl, Chem. Ber., 1962, 95, 2881), triethylorthoformate (90 ml) and acetic acid (90 ml) was heated from 60° to 65° over thirty minutes. After a further thirty minutes at 65°, the mixture was evaporated at 0.01 mm. The residue was suspended in ethanol (150 ml), cooled in ice and treated with isopropylamine (30 ml). After one hour, the precipitate was filtered off* and washed with ice-cold ethanol, then ether. This material (6.5 g out of 9.42 g obtained) was added to a stirred mixture of 5 N sodium hydroxide solution (65 ml) and ethanol (65 ml). After stirring for ten minutes at room temperature, the mixture was diluted with water and cooled. The precipitate was filtered off and dried to give Compound no 17 of Table I (3.55 g, m.p. 102°–104°).

*Using 2-aminopentane and 2-aminooctane, the intermediates were largely in solution at this stage. The filtrates were treated with sodium hydroxide solution. The products were extracted in dichloromethane, isolated by chromatography on silica gel using 50:50 cyclohexane/ether as eluant, then distilled in a bulb-tube apparatus. Physical characteristics were as shown in Table I.

Compounds nos 19 and 20 were prepared similarly using the appropriate amines but some modification to the method was necessary.

EXAMPLE 5

This Example illustrates the preparation of Compound no 21 of Table I.

A stirred mixture of Compound no 17 of Table I (8.37 g), 1 N sulphuric acid (84 ml) and acetic acid (42 ml) was cooled in ice and treated portionwise with finely ground potassium permanganate (4.2 g). After stirring vigorously for forty minutes, the mixture was diluted with water and decolourised with sodium metabisulphite. The precipitate was filtered off, washed well with water, dried and recrystallised from cyclohexane/petroleum (b.p. 60°–80°) to give the title compound (6.8 g, m.p. 111°–113°).

EXAMPLE 6

This Example illustrates the preparation of Compound no 22 of Table I.

A solution of Compound no 21 of Table I (1.8 g) in methanol (20 ml) containing sodium methoxide (from 0.21 g sodium) was refluxed for three hours and evaporated to dryness. The residue was triturated with water and the solid filtered off, washed with water and dried. Recrystallisation from cyclohexane/petroleum (b.p. 60°–80°) gave the title compound (1.25 g, m.p. 103°–106°).

EXAMPLE 7

An emulsifiable concentrate was made up by mixing the ingredients, and stirring the mixture until all the constituents were dissolved.

| | |
|---|---|
| Compound No 1 of Table I | 10% |
| Ethylene dichloride | 40% |
| Calcium dodecylbenzenesulphate | 5% |
| "Lubrol" L | 10% |
| "Aromasol" H | 35% |

EXAMPLE 8

A composition in the form of grains readily dispersible in a liquid, e.g. water, was prepared by grinding together the first three ingredients in the presence of added water and then mixing in the sodium acetate. The resultant mixture was dried and passed through a British Standard mesh sieve, size 44–100, to obtain the desired size of grains.

| | |
|---|---|
| Compound No 2 of Table I | 50% |
| "Dispersol" T | 25% |
| "Lubrol" APN 5 | 1.5% |
| Sodium acetate | 23.5% |

EXAMPLE 9

The ingredients were all ground together to produce a powder formulation readily dispersible in liquids.

| | |
|---|---|
| Compound No 3 of Table I | 45% |
| "Dispersol" T | 5% |
| "Lissapol" NX | 0.5% |
| "Cellofas" B600 | 2% |
| Sodium acetate | 47.5% |

EXAMPLE 10

The active ingredient was dissolved in a solvent and the resultant liquid was sprayed on to the granules of China clay. The solvent was then allowed to evaporate to produce a granular composition.

| | |
|---|---|
| Compound No 4 of Table I | 5% |
| China clay granules | 95% |

EXAMPLE 11

A composition suitable for use as a seed dressing was prepared by mixing the three ingredients.

| | |
|---|---|
| Compound No 5 of Table I | 50% |
| Mineral oil | 2% |
| China clay | 48% |

EXAMPLE 12

A dusting powder was prepared by mixing the active ingredient with talc.

| | |
|---|---|
| Compound No 6 of Table I | 5% |
| Talc | 95% |

EXAMPLE 13

A Col formulation was prepared by ball-milling the constituents set out below and then forming an aqueous suspension of the ground mixture with water.

| | |
|---|---|
| Compound No 7 of Table I | 40% |
| "Dispersol" T | 10% |
| "Lubrol" APN5 | 1% |
| Water | |

EXAMPLE 14

A dispersible powder formulation was made by mixing together the ingredients set out below and then grinding the mixture until all were thoroughly mixed.

| | |
|---|---|
| Compound No 8 of Table I | 25% |
| "Aerosol" OT/B | 2% |
| "Dispersol" A.C. | 5% |
| China clay | 28% |
| Silica | 40% |

EXAMPLE 15

This Example illustrates the preparation of a dispersible powder formulation. The ingredients were mixed and the mixture then ground in a comminution mill.

| | |
|---|---|
| Compound No 9 of Table I | 25% |
| "PERMINAL" BX | 1% |
| "Dispersol" T | 5% |
| Polyvinylpyrrolidone | 10% |
| Silica | 25% |
| China clay | 34% |

EXAMPLE 16

The ingredients set out below were formulated into a dispersible powder by mixing the grinding the ingredients.

| | |
|---|---|
| Compound No 11 of Table I | 25% |
| "Aerosol" OT/B | 2% |
| "Dispersol" A | 5% |
| China clay | 68% |

In Examples 2 to 11 the proportions of the ingredients given are by weight.

There now follows an explanation of the compositions or substances represented by the various Trade Marks and Trade Names mentioned above.

| | |
|---|---|
| LUBROL L : | a condensate of nonyl phenol (1 mole) with ethylene oxide (13 moles) |
| AROMASOL H : | a solvent mixture of alkylbenzenes |
| DISPERSOL T AND AC : | a mixture of sodium sulphate and a condensate of formaldehyde with sodium naphthalene sulphonate. |
| LUBROL APN 5 : | a condensate of nonyl phenol (1 mole) with naphthalene oxide (5.5 moles). |
| CELLOFAS B600 : | a sodium carboxymethyl cellulose thickener. |
| LISSAPOL NX : | A condensate of nonyl phenol (1 mole) with ethylene oxide (8 moles). |
| AEROSOL OT/B : | dioctyl sodium sulpho succinate. |
| PERMINAL BX : | a sodium alkyl naphthalene sulphonate. |

EXAMPLE 17

The isoxazolo [5,4-d] pyrimidine derivatives were tested against a variety of foliar fungal diseases of plants. The technique employed was as follows.

The plants were grown in John Innes Potting Compost (No. 1, or Seed, as appropriate) in 4 cm diameter mini-pots. A layer of fine sand was placed at the bottom of the pot to facilitate uptake of test compound by the roots.

The test compounds were formulated either by bead-milling with aqueous Dispersol T or as a solution in acetone/ethanol which was diluted to the required concentration immediately before use. For the tests conducted, 100 ppm a.i. suspensions were sprayed on to the foliage and applied to the roots of the same plant via the soil. (Sprays were applied to maximum retention, and root drenches to a final concentration equivalent to approximately 40 ppm a.i./dry soil). Tween 20, to give a final concentration of 0.1%, was added when the sprays were applied to the cereals.

For most of the tests, the test compound was applied to the soil (roots) and to the foliage (by spraying) one or two days before the plant was inoculated with the diseases. An exception was the test on *Erysiphe graminis*, in which the plants were inoculated 24 hours before treatment. After inoculation, the plants were put into an appropriate environment to allow infection to take place and then incubated until the disease was ready for assessment. The period between inoculation and assessment varied from 4 to 9 days according to the disease and environment, as shown in Table II below.

TABLE II

| DISEASE AND PLANT | INTERVAL USUAL TIME (DAYS)* |
|---|---|
| (1) *Puccinia recondita* (wheat) | 8-9 |
| (2) *Phytophthora infestans* (tomato) | 3 |
| (3) *Plasmopara viticola* (vine) | 6 |
| (4) *Piricularia oryzae* (rice) | 6 |
| (5) *Botrytis cinerea* (tomatoes) | 5 |
| (6) *Erysiphe graminis* (barley) | 7 |

*N.B. These intervals are not rigid and will vary with the individual tests. Assessment is normally done at the point of optimum disease development commensurate with a practical timetable.

The disease control was recorded by the following grading:
4 = No disease
3 = 0-5%
2 = 6-25%
1 = 26-60%
0 = >60%

The results are shown in Table III.

TABLE III

| COMPOUND NO | PUCCINIA RECONDITA (wheat) | PHYTOPHTHORA INFESTANS (tomato) | PLASMOPARA VITICOLA (vine) | PIRICULARIA ORYZAE (rice) | BOTRYTIS CINEREA (tomato) | ERYSIPHE GRAMINIS (barley) | CERCOSPORA ARACHIDICOLA (peanut) |
|---|---|---|---|---|---|---|---|
| 1 | 3 | | 4 | 2 | 2 | 4 | |
| 2 | 4 | 0 | 4 | 4 | — | — | |
| 3 | 4 | 4 | 3 | 3 | 0 | 4 | |
| 4 | 4 | 4 | 3 | 3 | 3 | 4 | |
| 5 | 4 | 4 | 3 | 3 | 0 | 4 | |
| 6 | 3 | 2 | 4 | 3 | 3 | 4 | |
| 7 | 3 | 3 | 4 | 3 | 0 | 4 | |
| 8 | 2 | 2 | 0 | 1 | 2 | 3 | |
| 9 | 3 | 3 | 4 | 3 | 1 | 4 | |
| 10 | 3 | 1 | 0 | 0 | 2 | 3 | |
| 11 | 3 | 4 | 4 | 1 | 2 | 3 | |
| 12 | 4 | 4 | 1 | 4 | 0 | 3 | |
| 13 | 0 | 1 | 0 | 0 | 1 | 0 | — |
| 14 | 0 | 0 | 0 | — | 1 | 1 | — |
| 15 | 2 | 1 | 0 | — | 2 | 3 | — |
| 16 | 3 | 4 | 4 | 3 | 0 | 0 | — |
| 17 | 2 | 3 | 0 | 3 | 0 | 3 | — |
| 18 | 1 | 2 | 0 | 0 | 0 | 2 | — |
| 19 | 1 | 2 | 0 | 0 | 1 | 3 | — |
| 20 | 0 | 3 | 0 | 0 | 0 | 1 | — |

TABLE III-continued

| COMPOUND NO | PUCCINIA RECONDITA (wheat) | PHYTOPHTHORA INFESTANS (tomato) | PLASMOPARA VITICOLA (vine) | PIRICULARIA ORYZAE (rice) | BOTRYTIS CINEREA (tomato) | ERYSIPHE GRAMINIS (barley) | CERCOSPORA ARACHIDICOLA (peanut) |
|---|---|---|---|---|---|---|---|
| 21 | 0 | 0 | 0 | 2 | 0 | 1 | 0 |
| 22 | 2 | 3 | 3 | 3 | 1 | 3 | 3 |
| 23 | 3 | 4 | 3 | 4 | 1 | 3 | 4 |
| 24 | 4 | 3 | 3 | 3 | 0 | 3 | 4 |
| 25 | 3 | 4 | 3 | 4 | 2 | 4 | 3 |
| 26 | 2 | 3 | 3 | 2 | 3 | 2 | 3 |
| 27 | 4 | 4 | 3 | 4 | 0 | 3 | 3 |
| 28 | 0 | 1 | 0 | 1 | 0 | 0 | 0 |
| 29 | — | 3 | 0 | 3 | 1 | — | — |
| 30 | 0 | 4 |  | 4 | 0 | 1 | 0 |
| 31 | 3 | 4 | 0 | 4 | 0 | 4 | 3 |
| 32 | 3 | 4 | 0 | 3 | 0 | 4 | 3 |
| 33 | 2 | 4 | 0 | 3 | 0 | 4 | 0 |

"—" signifies no test conducted.

We claim:
1. A process for combating pests selected from the group consisting of fungi, bacteria, insects and acarids, which comprises applying to plants, seeds, or their loci, a pesticidally effective amount of an isoxazolo [5,4-d] pyrimidine derivative having the formula:

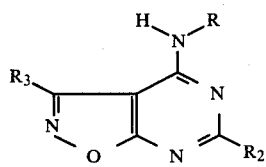

a salt, or optical isomer thereof, wherein R is a group selected from the class consisting of alkyl having from 3 to 10 carbon atoms, aralkyl, and alkoxyalkyl having up to 13 carbon atoms; $R_2$ is hydrogen or methyl; $R_3$ is methyl, ethyl, methoxy, methylsulphonyl, methylthio or phenyl.

2. A process according to claim 1 for combating fungi wherein R is

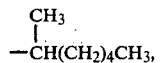

$R_2$ is hydrogen and $R_3$ is methyl.

3. A process according to claim 1 wherein said pests are fungi and said pyrimidine derivative is applied in a fungicidally effective amount.

4. A pesticidal composition for combating pests selected from the group consisting of fungi, bacteria, insects and acarids which comprises as an active ingredient an isoxazolo [5,4-d] pyrimidine derivative as defined in claim 1, said derivative being present in a pesticidally effective amount in combination with a carrier.

* * * * *